United States Patent
Tamanoi (10) Patent No.: US 11,191,836 B2
(45) Date of Patent: Dec. 7, 2021

(54) BIODEGRADABLE NANOCARRIER(S) (BPMOS) FOR NEUTRON CAPTURE THERAPY AND METHODS THEREOF

(71) Applicant: TAE Life Sciences, Foot Hill Ranch, CA (US)

(72) Inventor: Fuhuhiko Tamanoi, Kyoto (JP)

(73) Assignee: TAE Life Sciences, LLC, Foothill Ranch, CA (US)

( * ) Notice: Subject to any disclaimer, the term of this patent is extended or adjusted under 35 U.S.C. 154(b) by 0 days.

(21) Appl. No.: 16/501,741

(22) Filed: May 31, 2019

(65) Prior Publication Data

US 2019/0365898 A1     Dec. 5, 2019

Related U.S. Application Data (60) Provisional application No. 62/763,156, filed on Jun. 1, 2018.

(51) Int. Cl.
| | |
|---|---|
| *A61K 41/00* | (2020.01) |
| *A61K 47/69* | (2017.01) |
| *A61K 47/54* | (2017.01) |
| *A61N 5/10* | (2006.01) |
| *A61K 9/51* | (2006.01) |
| *B82Y 30/00* | (2011.01) |
| *B82Y 5/00* | (2011.01) |
| *B82Y 40/00* | (2011.01) |

(52) U.S. Cl.
CPC ........ *A61K 41/0095* (2013.01); *A61K 9/5123* (2013.01); *A61K 47/548* (2017.08); *A61K 47/6923* (2017.08); *A61N 5/10* (2013.01); *A61K 2121/00* (2013.01); *A61N 2005/109* (2013.01); *B82Y 5/00* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 5,328,678 A * | 7/1994 | Fujii ...................... | A61K 9/127 424/1.21 |
| 6,770,020 B2 | 8/2004 | De Stasio et al. | |
| 9,168,301 B2 | 10/2015 | Chou et al. | |
| 9,433,800 B2 | 9/2016 | Levy et al. | |
| 2006/0067941 A1 | 3/2006 | Buzatu et al. | |
| 2006/0127307 A1 * | 6/2006 | Canham .............. | A61K 9/0097 424/1.11 |
| 2007/0009441 A1 | 1/2007 | Erathodiyil et al. | |
| 2016/0024122 A1 | 1/2016 | Raines et al. | |
| 2017/0173364 A1 | 6/2017 | Hainfeld et al. | |
| 2017/0326236 A1 | 11/2017 | Niu et al. | |
| 2019/0022222 A1 | 1/2019 | Chen et al. | |

OTHER PUBLICATIONS

Barth, et al., A Realistic Appraisal of Boron Neutron Capture Therapy as a Cancer Treatment Modality, Cancer Commun. (2018) 38:36.
Mekaru, et al., Biodegradability of Disulfide-Organosilica Nanoparticles Evaluated by Soft x-ray Photoelectron Spectroscopy . . . , ACS Appl. Nano Mater. 2019, 2, 479-488.
Croissant, et al., Biodegradable Ethylene-Bis(Propyl)Disulfide-Based Periodic Mesoproous Organosilica Nanorods and Nanospheres . . . , Adv. Mater., 2014.
Achilli, et al., BNCT and Nanoparticles: A Long Way to Routine Clinical Method, Int. J. Med. Nano Res 2015, 2:1.
Hawthorne, Boron-Containing Compounds for Liposome-Mediated Tumor Localization and Application to Neutron . . . , Dept. of Energy, Office of Biological and Enviro Res. Apr. 4, 2005.
Barth, et al., Boron Delivery Agents for Neutron Capture Therapy in Cancer, Cancer Commubn. (2018) 38:35.
Zhu, et al., Boron Drug Delivery via Encapsulated Magnetic Nanocomposites: A New Approach for BNCT in Cancer . . . , J. Nanomaterials, vol. 2010, Art. ID. 409320 Mar. 12, 2010.
Prasetyanto, et al., Breakable Hybrid Organosilica Nanocapsules for Protein Delivery, Agnew. Chem. 2015, 127, pp. 1-6.
Vares, et al., Functionalized Mesoporous Silica Nanoparticles for Innovative Boron-Neutron Capture Therapy of Resistant Cancers, BioRxiv Preprint online Nov. 17, 2018, pp. 1-18.
Gao, et al., Nanostructured Boron Compounds for Boron Neutron Capture Therapy . . . , Boron Based Compounds 1st. Ed. John Wiley & Sons (2018) pp. 371-388.
Martin, Monoclonal Antibody Targeted Delivery of Boron Loaded Gold Nanoparticles to Pancreatic Cancer Cells . . . (2014) Honors Thesis Collection. 207. pp. 1-35.
Watermann, et al., Mesporous Silica Nanoparticles as Drug Delivery Vehicles in Cancer, Nanomaterials 2017, 7, 189.
Gritzay, Neutron Source for Neutron Capture Therapy of Cancer Tissues at Kyiv Research Reactor, STCU Workshop, Oct. 11-12, 2006, pp. 1-11.
Jiang, et al., Incorporation and Characterization of Boron Neutron Capture Agents into Mesoporous Silicon and Silicon Nanowires, Phys. Status Solidi A (Jun. 2009) pp. 1-4.
Matsuda, et al., Dose Distribution and Clinical Response of Glioblastoma Treated with Boron Neutron Capture therapy, App. Rad. & Iso. 67 (2009) S19-S21.
Abi-Ghaida, et al., Multifunctional Silica Nanoparticles Modifed via Silyated-Decaborate Precursors, J. Nanomaterials, vol. 2105, Art. ID 608432, pp. 1-8.
Maggini, et al., Breakable Msoporous Silica Nanoparticles for Targeted Drug Delivery, Electronic Supp. Mat. for ESI for Nanoscale, pp. 1-37 (2016).
Cirrone, et al., First Experimental Proof of Proton Boron Capture Therapy (PBCT) to Enhance Protontherapy Effectiveness, Sci. Rpts. (2018) 8:1141 (Jan. 18, 2018) pp. 1-15.

* cited by examiner

*Primary Examiner* — Jennifer Lamberski
(74) *Attorney, Agent, or Firm* — LOSMP; Shane M. Popp (57) ABSTRACT

Biodegradable Periodic Mesoporous Organosilica (BPMO) nanomaterials and methods of making BPMOs loaded with Neutron Capture Agents are disclosed herein. Consequently, the BPMOs loaded with Neutron Capture Agents provide a method of treating cancer, immunological disorders and other disease by utilizing a Neutron Capture Therapy modality.

15 Claims, 6 Drawing Sheets

Figure 1: Synthesis of BPMO loaded with $^{10}$BPA and surface modified with phosphonate

Figure 2: Characterization of BPMO nanoparticles (1) BPMO was analyzed by SEM (scanning electron microscopy) (a) and by TEM (b).

(2) Degradation of BPMO in GSH solution

Figure 3: Tumor targeting of BPA-loaded phosphonate modified BPMO

Figure 4: Tumor targeting of BPA-loaded phosphonate modified BPMO

Figure 6: Flowchart of Experimental Protocol Using BNCT with BPA-loaded BPMO in Chicken Egg Tumor Model

BIODEGRADABLE NANOCARRIER(S) (BPMOS) FOR NEUTRON CAPTURE THERAPY AND METHODS THEREOF

CROSS-REFERENCE TO RELATED APPLICATIONS

This application claims priority to U.S. Provisional Patent Application No. 62/763,156 filed 1 Jun. 2018, the contents of which are fully incorporated by reference herein.

STATEMENT OF RIGHTS TO INVENTIONS MADE UNDER FEDERALLY SPONSORED RESEARCH

Not applicable.

FIELD OF THE INVENTION

The invention described herein relates to the field of nanotechnology and cancer therapy. Specifically, the invention relates to biodegradable mesoporous silica nanoparticles used as a vehicle for neutron capture therapy in humans. The invention further relates to the treatment of cancers and other immunological disorders and diseases.

BACKGROUND OF THE INVENTION

Cancer is the second leading cause of human death next to coronary disease. Worldwide, millions of people die from cancer every year. In the United States alone, as reported by the American Cancer Society, cancer causes the death of well over a half-million people annually, with over 1.2 million new cases diagnosed per year. While deaths from heart disease have been declining significantly, those resulting from cancer generally are on the rise.

Worldwide, several cancers stand out as the leading killers. In particular, carcinomas of the lung, prostate, breast, colon, pancreas, ovary, and bladder represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Furthermore, many cancer patients experience a recurrence.

Although cancer therapy has improved over the past decades and survival rates increased, the heterogeneity of cancer still demands new therapeutic strategies utilizing a plurality of treatment modalities. This is especially true in treating solid tumors at anatomical crucial sites (e.g., glioblastoma, head and neck squamous cell carcinoma, and lung adenocarcinoma) which are sometimes limited to standard radiotherapy and/or chemotherapy. Nonetheless, detrimental effects of these therapies are chemo- and radioresistance, which promote locoregional recurrences, distant metastases and second primary tumors, in addition to severe side-effects that reduce the patients' quality of life.

Therefore, it is of utmost importance to develop new therapeutic strategies to overcome resistances and to reduce side-effects by targeted therapy. One possibility is to embrace the enhanced permeability and retention (EPR) effect of solid tumors. Due to a leaky vasculature and the lack of lymphatic drainage small structures such as nanoparticles can accumulate in the tumor. Therefore, exploiting nanoparticles as drug delivery vehicles is a promising approach.

Additionally, Neutron Capture Therapy (NCT) is a promising form of radiation therapy. Even though the conceptual techniques of NCT and specifically Boron Neutron Capture Therapy ("BNCT") is well known, the technological limitations associated with this type of treatment have slowed progress. However, given the technological improvements in both (i) the infusion or delivery of a capture compound, which preferably concentrates in the tumor, and (ii) the irradiation of the tumor site by neutrons, there has been a resurgence in NCT treatment methods.

From the aforementioned, it will be readily apparent to those skilled in the art that a new treatment paradigm is needed in the treatment of cancers and other immunological diseases. By using modern nanocarriers and optimized NCT modalities, a new disease treatment can be achieved with the overall goal of more effective treatment, reduced side effects, and lower production costs.

Given the current deficiencies associated with NCT, it is an object of the present invention to provide new and improved methods of treating cancer(s), immunological disorders, and other diseases utilizing nanocarriers and NCT.

SUMMARY OF THE INVENTION

The invention provides for nanomaterials fabricated for use as a drug delivery modality to treat human diseases such as cancer, immunological disorders, including but not limited to rheumatoid arthritis, ankylosing spondylitis, and other cellular diseases, including but not limited to Alzheimer's disease. In certain embodiments, the nanomaterials comprise mesoporous silica nanoparticles ("MSN" or "MSNs", as the case may be). In a further embodiment, an MSN of the invention comprises a bodegradable bond within the framework of the MSN. Generally speaking, and for the purposes of this invention, biodegradable MSNs tuned for biodegradation by incorporating disulfide, tetrasulfide bonds, or protease sensitive bonds are hereinafter referred as Biodegradable Periodic Mesoporous Organosilica ("BPMO" or "BPMOs", as the case may be).

In one embodiment, the surface of a BPMO is modified with phosphonate.

In another embodiment, a MSN or BPMO of the invention is loaded with a Neutron Capture Agent.

In a further embodiment, the Neutron Capture Agent comprises the Boron isotope $^{10}B$.

In a further embodiment, the Neutron Capture Agent comprises the Lithium isotope $^{6}Li$.

In a further embodiment, the Neutron Capture Agent comprises the He isotope $^{3}He$.

In a further embodiment, the Neutron Capture Agent comprises the Cadmium isotope $^{113}Cd$.

In a further embodiment, the Neutron Capture Agent comprises the Samarium isotope $^{149}Sm$.

In a further embodiment, the Neutron Capture Agent comprises the Gadolinium isotope $^{157}Gd$.

In a further embodiment, the Neutron Capture Agent comprises an isotope of Au (Gold).

In a further embodiment, the Neutron Capture Agent comprises an isotope with a favorable neutron capture cross section.

In a further embodiment, the invention comprises methods of concentrating neutrons in a cell comprising (i) loading a MSN and/or BPMO with a Neutron Capture Agent; (ii) administering the loaded MSN or BPMO to a patient, and (iii) irradiating the cell with neutrons.

In another embodiment, the present disclosure teaches methods of fabricating MSN and/or BPMOs with Neutron Capture Agents.

In another embodiment, the present disclosure teaches methods of treating cancer(s), immunological disorders and other diseases in humans.

DETAILED DESCRIPTION OF THE INVENTION

Outline of Sections
I.) Definitions
II.) Mesoporous Silica Nanoparticles (MSN) & Periodic Mesoporous Organosilica (PMO)
III.) Neutron Capture Agents
IV.) PMOs loaded with Neutron Capture Agents
V.) Boron Neutron Capture Therapy
VI.) Methods of Delivering Neutron Capture Agents to a Cell
VII.) Methods of Treating Cancer(s) and Other Immunological Disorder(s)
VIII.) KITS/Articles of Manufacture I.) Definitions Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art.

When a trade name is used herein, reference to the trade name also refers to the product formulation, the generic drug, and the active pharmaceutical ingredient(s) of the trade name product, unless otherwise indicated by context.

The terms "advanced cancer", "locally advanced cancer", "advanced disease" and "locally advanced disease" mean cancers that have extended through the relevant tissue capsule, and are meant to include stage C disease under the American Urological Association (AUA) system, stage C1-C2 disease under the Whitmore-Jewett system, and stage T3-T4 and N+ disease under the TNM (tumor, node, metastasis) system. In general, surgery is not recommended for patients with locally advanced disease, and these patients have substantially less favorable outcomes compared to patients having clinically localized (organ-confined) cancer.

The terms "inhibit" or "inhibition of" as used herein means to reduce by a measurable amount, or to prevent entirely.

The term "mammal" refers to any organism classified as a mammal, including mice, rats, rabbits, dogs, cats, cows, horses and humans. In one embodiment of the invention, the mammal is a mouse. In another embodiment of the invention, the mammal is a human.

The terms "metastatic cancer" and "metastatic disease" mean cancers that have spread to regional lymph nodes or to distant sites, and are meant to include stage D disease under the AUA system and stage T×N×M+ under the TNM system.

"molecular recognition" means a chemical event in which a host molecule is able to form a complex with a second molecule (i.e. the guest). This process occurs through non-covalent chemical bonds, including but not limited to, hydrogen bonding, hydrophobic interactions, ionic interaction.

"Pharmaceutically acceptable" refers to a non-toxic, inert, and/or composition that is physiologically compatible with humans or other mammals.

"Nanomaterial" means a material in any dimensional form (zero, one, two, three) and domain size in the range 40-400 nanometers.

"Nanostructure" means a structure having at least one dimension that is less than 500 nanometers. Examples, include but are not limited to nanocrystals, nanocomposites, nanograins, nanotubes, nanoceramics, and nanopowders.

"Nanofiller" (a.k.a. nanostructured filler) means a structure or particle intimately mixed with a matrix to form a nanostructured composite. At least one of the nanostructured filler and the nanostructured composite has a desired material property which differs by at least 20% from the same material property for a micron-scale filler or a micron-scale composite, respectively. The desired material property is selected from the group consisting of refractive index, transparency to light, reflection characteristics, resistivity, permittivity, permeability, coercivity, B-H product, magnetic hysteresis, breakdown voltage, skin depth, curie temperature, dissipation factor, work function, band gap, electromagnetic shielding effectiveness, radiation hardness, chemical reactivity, thermal conductivity, temperature coefficient of an electrical property, voltage coefficient of an electrical property, thermal shock resistance, biocompatibility and wear rate. The nanostructured filler may comprise one or more elements selected from the s, p, d, and f groups of the periodic table, or it may comprise a compound of one or more such elements with one or more suitable anions, such as aluminum, antimony, boron, bromine, carbon, chlorine, fluorine, germanium, hydrogen, indium, iodine, nickel, nitrogen, oxygen, phosphorus, selenium, silicon, sulfur, or tellurium. The matrix may be a polymer (e.g., poly(methyl methacrylate), poly(vinyl alcohol), polycarbonate, polyalkene, or polyaryl), a ceramic (e.g., zinc oxide, indium-tin oxide, hafnium carbide, or ferrite), or a metal (e.g., copper, tin, zinc, or iron). Loadings of the nanofiller may be as high as 95%, although loadings of 80% or less are preferred. The invention also comprises devices which incorporate the nanofiller (e.g., electrical, magnetic, optical, biomedical, and electrochemical devices).

The term "neutron capture agent" means a stable non-reactive chemical isotope which, when activated by neutrons produces alpha-rays and gamma-rays.

The term "neutron capture therapy" means a noninvasive therapeutic modality for treating locally invasive malignant tumors such as primary brain tumors and recurrent head and neck cancer and other immunological disorders and disease by irradiating a neutron capture agent with neutrons.

As used herein "to treat" or "therapeutic" and grammatically related terms, refer to any improvement of any consequence of disease, such as prolonged survival, less morbidity, and/or a lessening of side effects which are the byproducts of an alternative therapeutic modality; as is readily appreciated in the art, full eradication of disease is a preferred but albeit not a requirement for a treatment act.

II.) Mesoporous Silica Nanoparticles (MSN) & Biodegradable Periodic Mesoporous Organosilica (BPMO)

Mesoporous silica nanoparticles (MSNs) have emerged as a powerful drug delivery vehicle. Generally, these silica particles have a diameter ranging from 40 to 400 nm and contain thousands of pores where anticancer drugs, among other things, can be stored. Various cellular and animal studies have been reported that point to the efficacy of MSNs to deliver anticancer drugs. See, for example, Wang, Y. et. al., Mesoporous silica nanoparticles in drug delivery and biomedical applications. *Nanomedicine.* 11, 313-327 (2015). Because of the relative stability of these nanomaterials, various chemical modifications can be applied to these nanoparticles. A surface charge property can be altered to prevent the aggregation of particles in biological media and to achieve prolonged circulation. Furthermore, various nanomachines can be engineered on the particle surface to confer the ability to release anticancer drug upon stimuli including light and magnetic field exposure.

Artisans skilled in the art have recently developed a new generation of mesoporous nanoparticles called biodegradable PMO (Periodic Mesoporous Organosilica) nanoparticles ("BPMO") which are tuned for biodegradation by incorporating disulfide, tetrasulfide bonds, or protease sensitive bonds leading to excellent candidates for nanomedicine applications. See, for example, Croissant, J. et. al., Biodegradable oxamide-phenylene-based mesoporous organosilica nanoparticles with unprecedented drug payloads for delivery in cells. *Chem. Eur. J.* 22, 14806-14811 (2016). These nanoparticles retain the advantageous features of MSNs described above and, in addition, they possess enhanced degradability. The BPMOs exhibit efficient loading capacity with Neutron Capture Agents, such as Boron, as well as other anticancer drugs, which are known in the art, and the Neutron Capture Agents can be delivered into human cancer cells.

A recently developed BPMOs contain biodegradable bonds within the framework of mesoporous silica network and thus are degradable by conditions inside the cell, such as reducing environment. For this, two (2) types of BPMO nanoparticles containing a disulfide bond or tetrasulfide bond have been developed. In a preferred embodiment, a BPMO of the invention is synthesized using the sol-gel synthesis method with precursors containing disulfide or tetrasulfide bond. The use of these special precursors for synthesis results in the incorporation of these biodegradable bonds into the framework of nanoparticles.

During the synthesis, surfactant CTAB (cetyltrimethylammonium bromide) was included to produce a porous structure. Generally speaking, a preferred BPMO of the invention was synthesized by mixing bis(triethoxysilylpropyl)disulfide with bis(triethoxysilyl)ethylene (50-50 ratio). The resulting BPMOs have a diameter of 100-300 nm and contain pores with 2-3.5 nm diameter.

In yet another preferred embodiment, a BPMO of the disclosure was synthesized by mixing 1,2-bis(triethoxysilyl)ethane with CTAB and NaOH, stirred vigorously and then the mixture was heated to 80° C. Next, the solution was added dropwise into the flask and bis[3(triethoxysilyl) propyl]tetrasulfide was added immediately thereafter. After condensation at 80° C. for 2.0 hours, BPMO was collected by centrifugation and washed twice with ethanol. To remove CTAB from the pores, the particles was refluxed overnight in ethanolic acid of ammonium nitrate. The particles were purified by washing with ethanol (3 times) and dried completely.

In yet another preferred embodiment, a BPMO of the present disclosure was functionalized with GOPTS (3-glycidyloxypropyl trimethoxysilane) by a post-synthesis grafting method. To open the epoxy ring of GOPTS, the functionalized BPMO was suspended in water and heated at 70° C. for two days. This step produces diol-modified BPMO. Further modification to add phosphonate on the surface was accomplished using 3(trihydroxylsilyl) propyl methyl phosphonate. $^{10}$BPA (4 borono L-phenylalanine) was added to the nanoparticles so that $^{10}$BPA will be chelated onto the diol modified BPMO.

In another preferred embodiment, a BPMO which has been surface modified with phosphonate is loaded with a Neutron Capture Agent, whereby the Neutron Capture Agent is encapsulated within the BPMO. In a further embodiment, the Neutron Capture Agent is chemically bonded to the surface of a BPMO. Exemplary embodiments of a Neutron Capture Agent of the invention is set forth herein.

One of ordinary skill in the art will appreciate and be enabled to make variations and modifications to the disclosed embodiment without altering the function and purpose of the invention disclosed herein. Such variations and modifications are intended within the scope of the present disclosure.

III.) Neutron Capture Agent(s)

Another aspect of the present invention relates to improved Neutron Capture Agents. Generally speaking, Neutron Capture Agents success is predicated on selective localization in tumor cells and adequate flux of neutrons of appropriate energy to the tumor. A current drawback with neutron capture therapy is the inability of neutron capture agents to adequately concentrate in the tumor, while at the same time minimizing concentration in normal cells. As will be appreciated by one of ordinary skill in the art, several neutron capture agents of the invention possess properties which will be beneficial for the instant disclosure. For example, a high cross section of thermal neutron interactions will cause high ionization capability whereby cells enriched by neutron capture agents will be killed and the normal cells will be damaged much less. However, to date, the diminishment of damaging healthy normal cells has not been achieved. It is an object of the present invention to remedy this deficiency.

In a further embodiment, the Neutron Capture Agent comprises the Boron isotope $^{10}$B.

In a further embodiment, the Neutron Capture Agent comprises the Lithium isotope $^{6}$Li.

In a further embodiment, the Neutron Capture Agent comprises the He isotope $^{3}$He.

In a further embodiment, the Neutron Capture Agent comprises the Cadmium isotope $^{113}$Cd.

In a further embodiment, the Neutron Capture Agent comprises the Samarium isotope $^{149}$Sm.

In a further embodiment, the Neutron Capture Agent comprises the Gadolinium isotope $^{157}$Gd.

In a further embodiment, the Neutron Capture Agent comprises an isotope of Au (Gold).

In a further embodiment, the Neutron Capture Agent comprises an isotope with a favorable neutron capture cross section.

One of ordinary skill in the art will appreciate and be enabled to make variations and modifications to the disclosed embodiment without altering the function and purpose of the invention disclosed herein. Such variations and modifications are intended within the scope of the present disclosure.

IV.) BPMOs Loaded with Neutron Capture Agents

One aspect of the present invention relates to BPMOs loaded with Neutron Capture Agents. As previously discussed, BPMOs of the disclosure have a high loading capacity at the appropriate pH. In a preferred embodiment, the pH is around 8.5. Furthermore, the once loaded, the Neutron Capture Agent is between 20%-60% to total weight of BPMO. In a preferred embodiment, the Neutron Capture Agent constitutes between. 30%-50% of the total weight of the loaded BPMO. In a further embodiment, the Neutron Capture Agent comprises the Boron isotope $^{10}$B. In a further embodiment, the Neutron Capture Agent comprises $^{10}$BPA. In a further embodiment, the Neutron Capture Agent comprises the Lithium isotope $^{6}$Li. In a further embodiment, the Neutron Capture Agent comprises the He isotope $^{3}$He. In a further embodiment, the Neutron Capture Agent comprises the Cadmium isotope $^{113}$Cd. In a further embodiment, the Neutron Capture Agent comprises the Samarium isotope $^{149}$Sm. In a further embodiment, the Neutron Capture Agent comprises the Gadolinium isotope $^{157}$Gd.

It will be appreciated by one or ordinary skill in the art that a Neutron Capture Agent may be fabricated to a PMO by various means known in the art, such as encapsulation, or chemically bonded to the surface of the BPMO, and/or conjugated to BPMOs using methods known in the art. Such variations and modifications are intended within the scope of the present disclosure.

V.) Boron Neutron Capture Therapy Using BPMOs Loaded with $^{10}$B

One aspect of the present disclosure is the use of BPMOs loaded with $^{10}$B as a modality for Boron Neutron Capture Therapy ("BNCT"). Briefly, BNCT is a binary treatment modality in which neither component alone is legal or highly toxic. The two components comprise (i) the infusion or delivery of a capture compound, which preferentially is concentrated in the tumor, and (ii) the irradiation of the tumor site by neutrons. Given the large cross-section of thermal neutron interactions with $^{10}$B, there is consequently a high probability of a splitting of Boron nucleus into He and Li. Given that the ionization capability of He and Li is high, and the runs are short, then the cells preferably enriched by Boron are killed and the healthy cells are damaged much less. Given this, the advantage of BNCT is the destruction of tumor cells without a highly traumatic surgical procedure. However, as will be understood by one of skill in the art, success is predicated high concentration and selective localization of $^{10}$B in tumor cells.

In one embodiment, $^{10}$B is loaded to a BPMO of the invention and is localized into a tumor cell. The BPMOs containing $^{10}$B are concentrated into the tumor and the tumor is irradiated using epithermal neutrons. The tumor cells are destroyed.

VI. Methods of Delivering Neutron Capture Agents to a Cell

As will be appreciated by one of ordinary skill in the art, the ability to efficiently deliver an improved Neutron Capture Agent of the present disclosure to a cell is an advantage of the present invention.

It is shown that the nanoparticle formulation (BPMOs of the present disclosure) enables a higher amount of Neutron Capture Agents to be administered safely to mammals. Briefly, to investigate tumor delivery of Neutron Capture Agents, it is shown by fluorescence of Neutron Capture Agents in the tumor from one (1) to five (5) days after injection of Neutron Capture Agents loaded PMO nanoparticles. The fluorescence is observed in the tumor. To examine whether the fluorescence is observed predominantly in the tumor, various organs are removed, processed and examined by fluorescence microscopy or other detection methods known in the art. It is shown that fluorescence is observed predominantly in the tumor whereas little fluorescence is observed in various organs. Control tumor represents tumor sample obtained from the model that did not receive nanoparticle injection. Thus, Neutron Capture Agents can be delivered preferentially in the tumor.

Furthermore, to investigate whether the BPMOs are localized to the tumor, it is shown that synthesized BPMO nanoparticles labeled with Rhodamine-B is prepared. Briefly, Rhodamine B labeled BPMO nanoparticles are prepared by the co-condensation with Rhodamine B-APTES prepared by chemically linking fluorescent Rhodamine B isothiocyanate (RBITC) dye with aminopropyltriethoxysilane (APTES) or other methods known in the art. These enable characterization of BPMO biodistribution by following red fluorescence. Rhodamine B labeled nanoparticles are injected and the distribution of red fluorescence is examined 1-3 days after the injection. Tumor and various organs from the sample are cut out. It is shown that red fluorescence was detected predominantly in the tumor two to three days after the injection. Much less red fluorescence was detected in other organs such as liver. The control tumor represents tumor sample obtained from the model that did not receive BPMO injection. Similar results are obtained when the analysis is carried out one day after the injection. Thus, BPMO nanoparticles preferentially accumulate in the tumor. On the other hand, BPMO surface modified to possess positive charge accumulated more in liver and kidney.

Accordingly, it is shown that BPMOs of the disclosure loaded with Neutron Capture Agents can be modified to selectively localize in high concentrations in tumor cells.

IX.) Kits/Articles of Manufacture

For use in the laboratory, prognostic, prophylactic, diagnostic and therapeutic applications described herein, kits are within the scope of the invention. Such kits can comprise a carrier, package, or container that is compartmentalized to receive one or more containers such as vials, tubes, and the like, each of the container(s) comprising one of the separate elements to be used in the method, along with a label or insert comprising instructions for use, such as a use described herein. For example, the container(s) can comprise a BPMO that is or can be detectably labeled and/or is loaded with a Neutron Capture Agent. Kits can comprise a container comprising a drug unit. The kit can include all or part of the BPMOs and/or Neutron Capture Agents.

The kit of the invention will typically comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapy or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as a cancer or other immunological disorder.

The terms "kit" and "article of manufacture" can be used as synonyms.

In another embodiment of the invention, an article(s) of manufacture containing compositions, such as BPMOs and/or Neutron Capture Agents and/or BPMOs loaded with Neutron Capture Agents. The article of manufacture typically comprises at least one container and at least one label. Suitable containers include, for example, bottles, vials, syringes, and test tubes. The containers can be formed from a variety of materials such as glass, metal or plastic. The container can hold BPMOs and Neutron Capture Agents.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agents in the composition can be a BPMO loaded with a Neutron Capture Agent.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples that follow, none of which is intended to limit the scope of the invention.

Example 1: Synthesis of BPMO

In one embodiment, a BPMO of the disclosure was synthesized in the following manner. First, 1,2-bis(triethoxysilyl)ethane was mixed with CTAB and NaOH, stirred vigorously, and then the mixture was heated to 80° C. Next, the solution was added dropwise into the flask and bis[3 (triethoxysilyl) propyl]tetrasulfide was added immediately thereafter. After condensation at 80° C. for 2.0 hours, BPMO was collected by centrifugation and washed twice with ethanol. Removal of the CTAB from the pores was performed by reflux overnight in ethanolic acid of ammonium nitrate. The particles were purified by washing with ethanol (3× times) and dried completely. See, FIG. 1.

Example 2: Characterization of BPMO Nanoparticles

Figure 2:
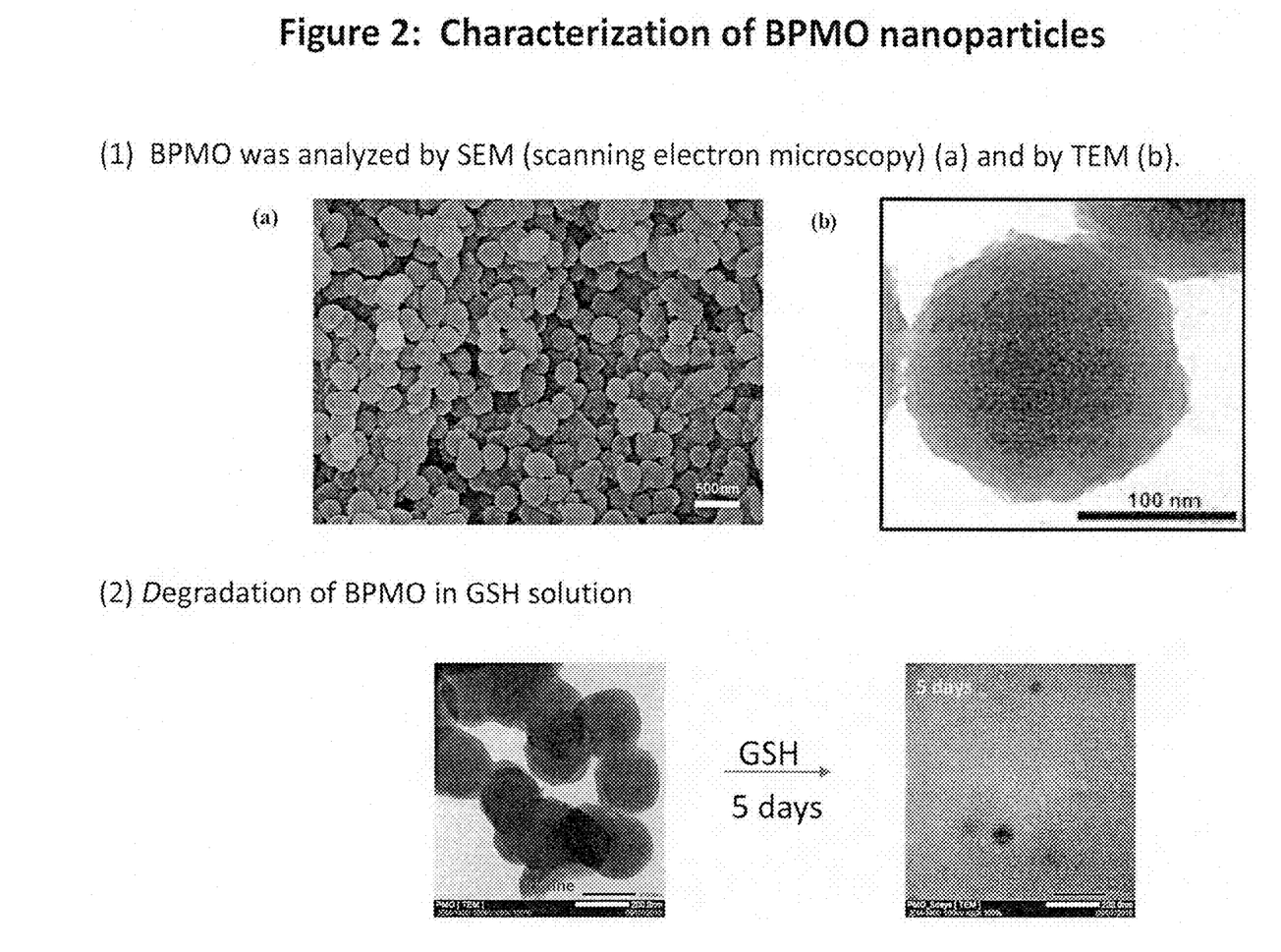
FIG. 2. Characterization of BPMO nanoparticles. (1)(a) shows the BPMO of the invention analyzed by SEM. (1)(b) shows the BPMO of the invention analyzed by TEM. (2) shows degradation analysis performed on the BPMO using TEM.

The BPMO's set forth in Example 1 (Synthesis of BPMO) were characterized by scanning electron microscopy ("SEM") and transmission electron microscopy ("TEM") using techniques known in the art. Analysis of the BPMO using SEM shows homogeneous nanoparticles with 100-200 nm diameter. See, FIG. 2(1)(a).

Analysis of the BPMO using TEM shows the presence of pore structure(s). See, FIG. 2(1)(b).

Finally, degradation analysis on the BPMO was performed using TEM. Briefly, BPMO (0.1 mg/ml) was incubated in PBS (phosphate buffered saline) solution containing 10 mM glutathione (GSH) at 37° C. for 5 days and visualized by TEM (transmission electron microscopy). The results show that BPMO was degradable under reducing conditions. See, FIG. 2(2).

Example 3: Synthesis of BPMO Surface Modified with Phosphonate and Diol

Figure 1:
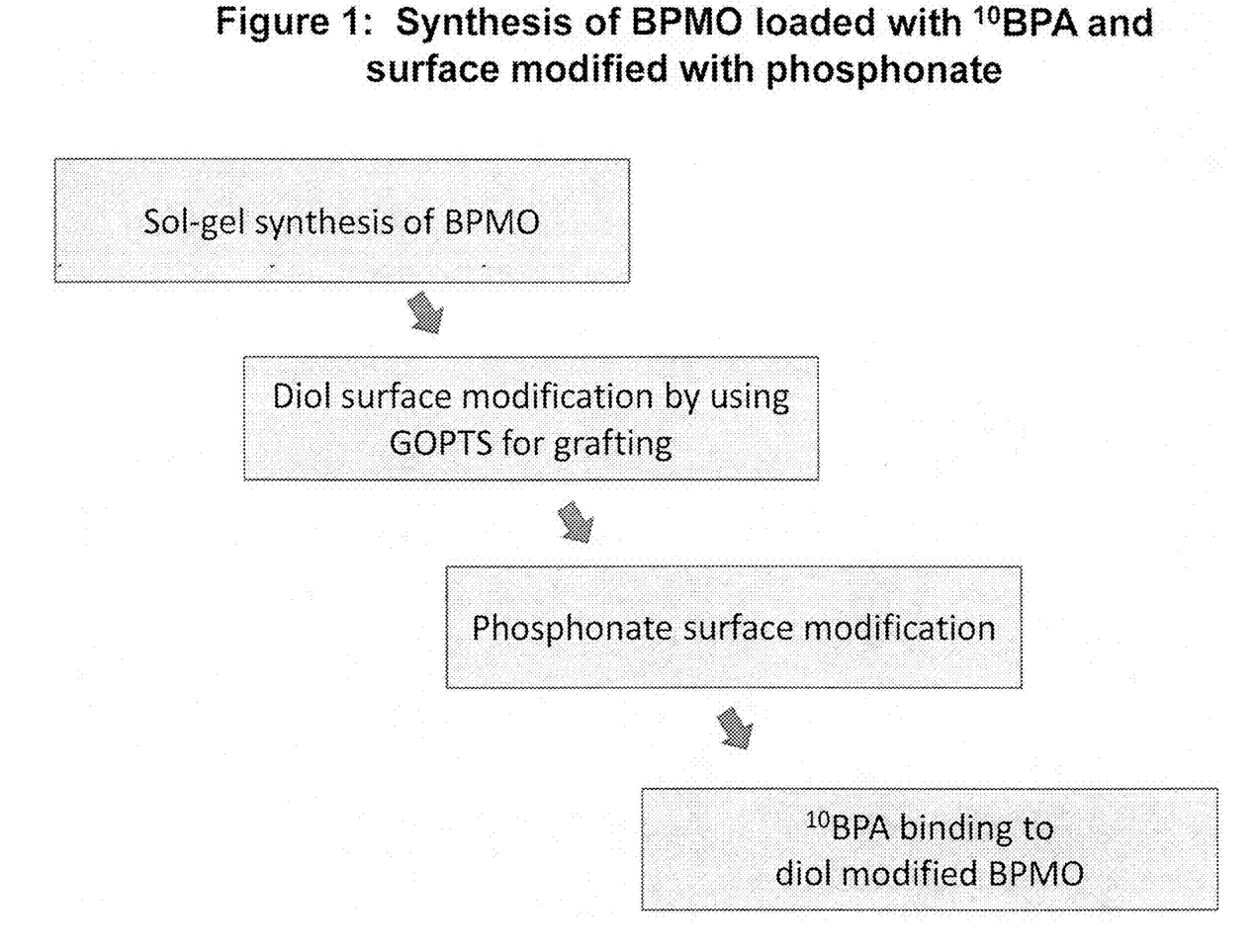
FIG. 1. Synthesis of BPMO loaded with $^{10}$BPA and surface modified with phosphonate.

The BPMO produced according to the example entitled "Synthesis of BPMO" was surface modified. Briefly, synthesized BPMO was immersed in toluene and the mixture was sonicated for 10 minutes. Then, 3-glycidyloxypropyl trimethoxysilane (GOPTS):

was added to this mixture and refluxed overnight. Solid product was collected by centrifugation and washed 3× times with ethanol. Dried product was obtained and added into deionized water. This mixture was heated at 70° C. for two (2) days. Diol-BPMO was further modified with 3(trihydroxysilyl) propyl methyl phosphonate to provide a negative charge on the surface by stirring the 3(trihydroxysilyl) propyl methyl phosphonate at 70° C. See, FIG. 1.

Example 4: Method of Loading $^{10}$BPA to Surface Modified BPMO

The BPMO functionalized with diol and phosphonate as described in the example entitled "Synthesis of BPMO surface modified with phosphonate and diol" was loaded with neutron capture agent $^{10}$BPA. Briefly, BPMO-diol was added into $^{10}$BPA solution, pH was adjusted to approximately 8.5-8.8 and the mixture was stirred at 40° C. for twenty-four (24) hr. The product was collected by centrifugation and then washed with deionized water and ethanol. Dried product was obtained after evaporation. The resulting composition P-BPMO-diol-$^{10}$BPA is shown by the process described in FIG. 1 and is within the scope of the invention.

Example 5: Tumor Targeting of $^{10}$BPA Loaded Phosphonate Modified BPMO

Evaluation of the BPMO set forth in the previous examples was carried out to show the tumor targeting activity of the $^{10}$BPA loaded BPMO. Briefly, fertilized eggs were incubated for ten (10) days at which time human cancer cells were transplanted onto the CAM membrane (chorioallantoic membrane). GFP expressing ovarian cancer cells are used. Three (3) days later, a tumor is formed on the CAM membrane. Rhodamine-B labeled BPMO synthesized as described in Example 2 is injected intravenously and the overlap of red fluorescence (BPMO) abd green fluorescence (GFP expressing tumor) are investigated.

Figure 3:
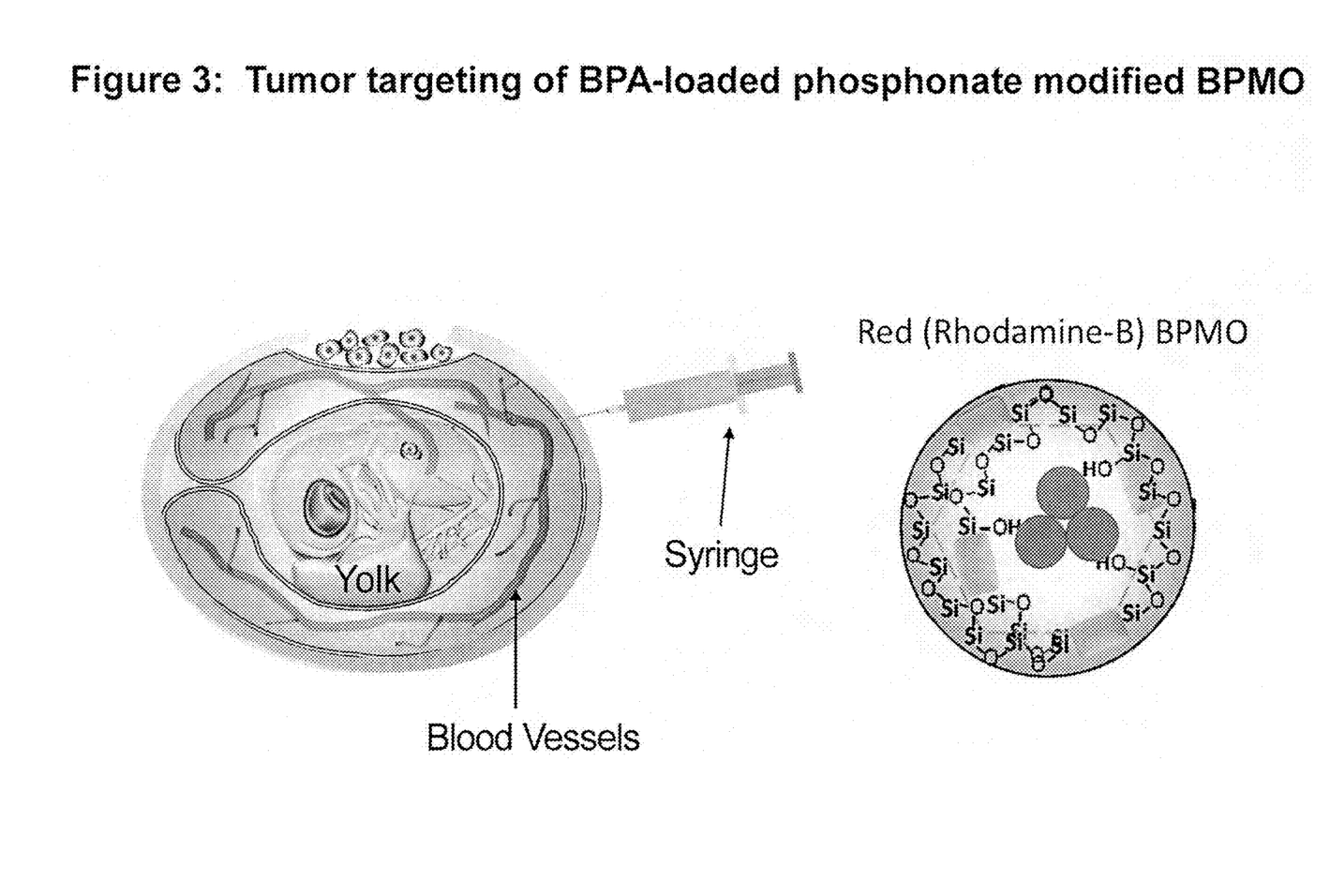
FIG. 3. A scheme to evaluate tumor targeting of BPA-loaded phosphonate modified BPMO.

The results demonstrate that $^{10}$BPA-loaded BPMO accumulates in the tumor when injected at 0.2 mg per egg intravenously. Two (2) days after the injection, the tumor as well as various organs from chick embryo were cut out and examined under fluorescent microscopy using techniques known in the art. Note that red fluorescence of BPMO overlaps with green fluorescence of tumor. See, FIG. 3 and FIG. 4.

Figure 4:
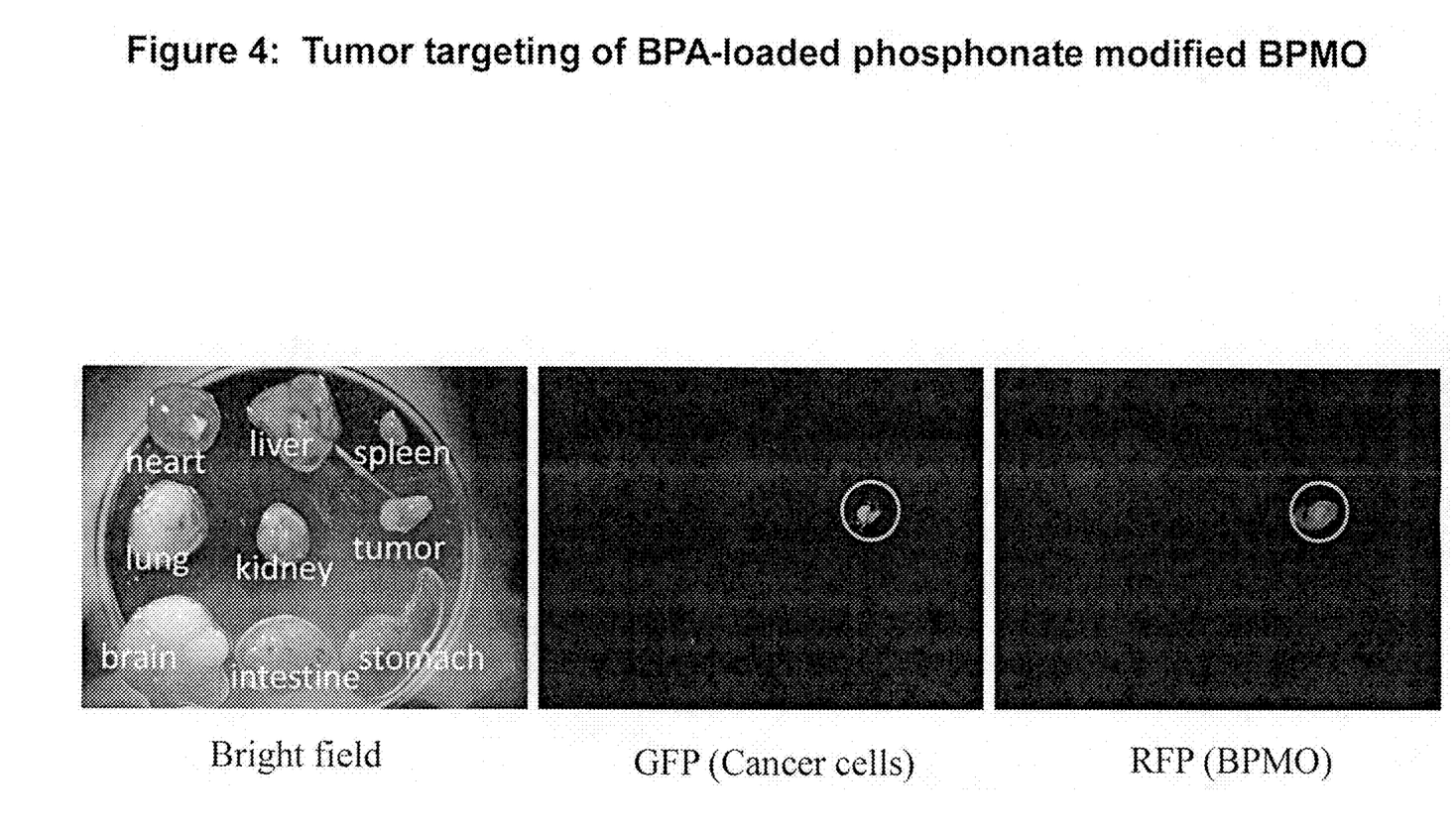
FIG. 4. Tumor targeting of BPA-loaded phosphonate modified BPMO.
Figure 5:
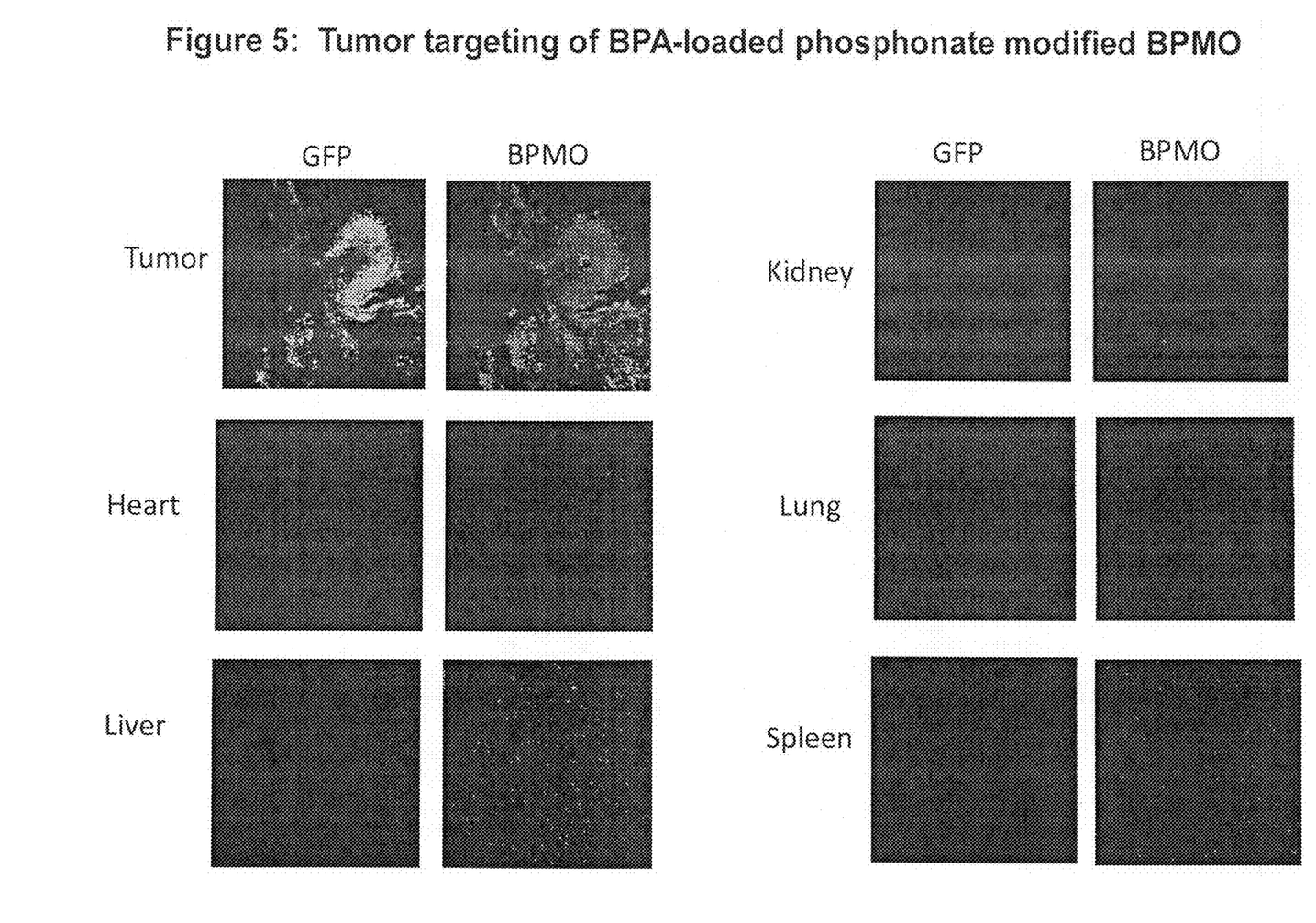
FIG. 5. Tumor targeting of BPA-loaded phosphonate modified BPMO.

In a subsequent analysis, the tumor and organs used and shown in FIG. 4 were cut into thin sections and then were examined by confocal microscopy using techniques known in the art. The results show that red fluorescence of BPMO is detected in the tumor with a de minimus amount in normal liver. Green fluorescence of tumor is due to GFP expressing cancer cells. See, FIG. 4 and FIG. 5.

Example 6: BNCT Using $^{10}$BPA Loaded BPMO Surface Modified with Phosphonate

Figure 6:
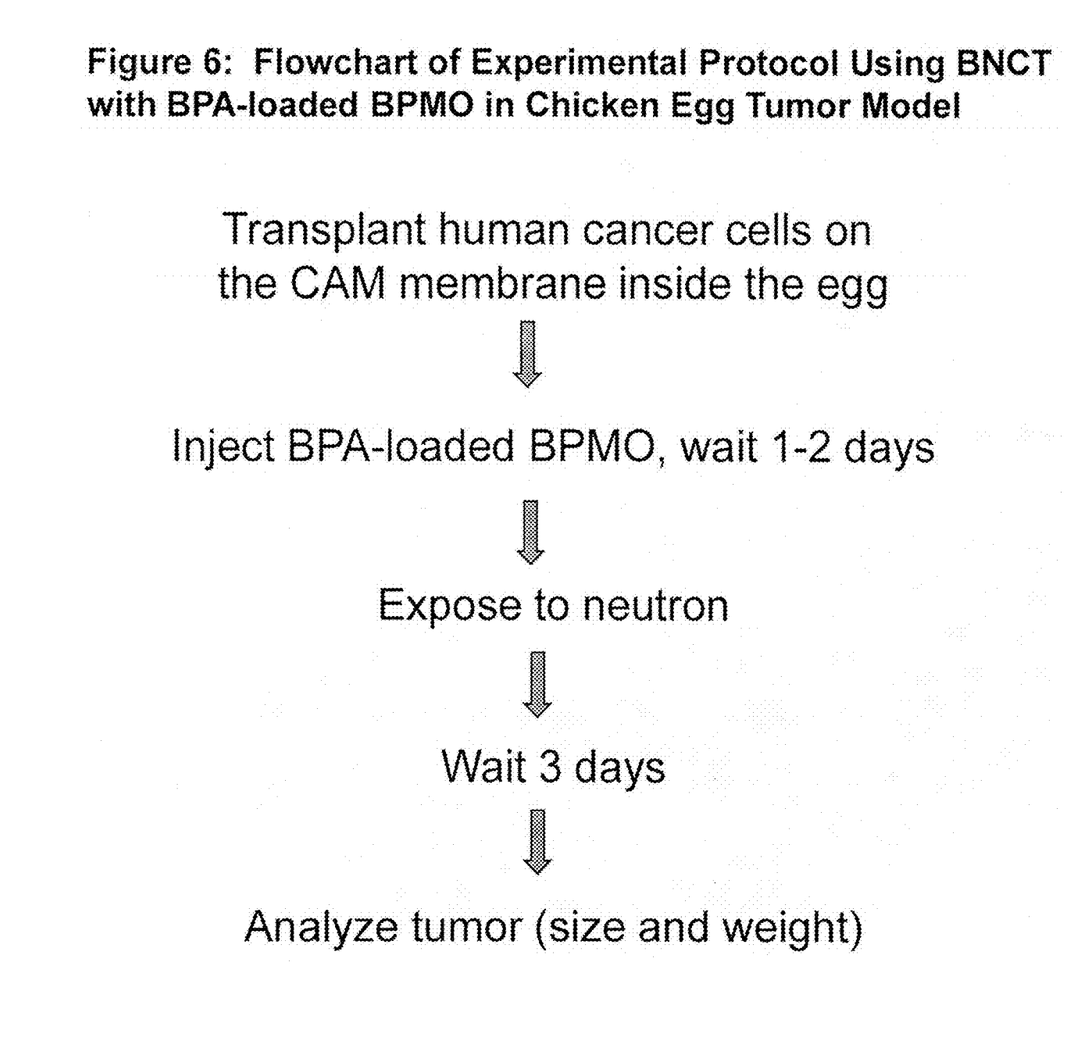
FIG. 6. Flowchart of Experimental Protocol Using BNCT with BPA-loaded BPMO in Chicken Egg Tumor Model.

The effectiveness of $^{10}$BPA loaded BPMO that has been surface modified with phosphonate as a therapeutic modality in BNCT is shown using the following method. First, human cancer cells are transplanted on the CAM membrane inside the chicken egg. Second, the 10BPA loaded BPMO that has been surface modified with phosphonate is injected and is allowed to set for 1-2 days. Exposure to a neutron beam is initiated. After exposure to the neutron (usually around 60 min), the chicken eggs are incubated for three (3) days. After three (3) days the tumor is analyzed with techniques known in the art and the size and weight of the tumor are measured. The tumor size and weight is examined. See, FIG. 6.

It will be understood by one of ordinary skill in the art that a variety of additional neutron capture agents can be utilized using the same protocol as described herein.

Example 7: Human Clinical Trials for the Treatment of Human Carcinomas Through the Use of BPMOs Loaded with Neutron Capture Agents BPMOs loaded with Neutron Capture Agents are used in accordance with the present invention which specifically accumulate in a tumor cell, and are used in the treatment of certain tumors and other immunological disorders and/or other diseases. In connection with each of these indications, two clinical approaches are successfully pursued.

I.) Adjunctive therapy: In adjunctive therapy, patients are treated with BPMOs loaded with Neutron Capture Agents in combination with a chemotherapeutic or pharmaceutical or biopharmaceutical agent or a combination thereof. Primary cancer targets, are treated under standard protocols by the addition of BPMOs loaded with Neutron Capture Agents and then irradiated. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents. These dosage reductions allow additional and/or prolonged therapy by reducing dose-related toxicity of the chemotherapeutic or biologic agent.

II.) Monotherapy: In connection with the use of the BPMOs loaded with Neutron Capture Agents in monotherapy of tumors, the BPMOs loaded with Neutron Capture Agents are administered to patients without a chemotherapeutic or pharmaceutical or biological agent. In one embodiment, monotherapy is conducted clinically in end-stage cancer patients with extensive metastatic disease. Protocol designs address effectiveness as assessed by the following examples, including but not limited to, reduction in tumor mass of primary or metastatic lesions, increased progression free survival, overall survival, improvement of patients health, disease stabilization, as well as the ability to reduce usual doses of standard chemotherapy and other biologic agents.

Dosage

Dosage regimens may be adjusted to provide the optimum desired response. For example, a single injection of loaded BPMOs may be administered, several divided doses may be administered over time or the dose may be proportionally reduced or increased as indicated by the exigencies of the therapeutic situation. "Dosage Unit Form" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the BPMO loaded with the Neutron Capture Agent, the individual mechanics of the irradiation mechanism (reactor) and the particular therapeutic or prophylactic effect to be achieved, and (b) the limitations inherent in the art of compounding such an compound for the treatment of sensitivity in individuals.

Clinical Development Plan (CDP)

The CDP follows and develops treatments of using BPMOs loaded with Neutron Capture Agents which are then irradiated using Neutron Capture Therapy in connection with adjunctive therapy or monotherapy. Trials initially demonstrate safety and thereafter confirm efficacy in repeat doses. Trials are open label comparing standard chemotherapy with standard therapy plus BPMOs loaded with Neutron Capture Agents which are then irradiated using Neutron Capture Therapy. As will be appreciated, one non-limiting criteria that can be utilized in connection with enrollment of patients is concentration of Neutron Capture Agents in a tumor as determined by standard detection methods known in the art.

The present invention is not to be limited in scope by the embodiments disclosed herein, which are intended as single illustrations of individual aspects of the invention, and any that are functionally equivalent are within the scope of the invention. Various modifications to the models, methods, and life cycle methodology of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A composition comprising:
   a) a biodegradable periodic mesoporous organosilica (BPMO) nanomaterial, wherein the BPMO is modified with a disulfide bond, a tetrasulfide bond, or a protease sensitive bond and wherein the BPMO surface is modified with phosphonate; and b) a neutron capture agent.

2. A composition comprising:
a) a biodegradable periodic mesoporous organosilica (BPMO) nanomaterial, wherein the BPMO is modified with a disulfide bond, a tetrasulfide bond, or a protease sensitive bond and wherein the BPMO surface is modified with phosphonate and diol; and
b) a neutron capture agent.

3. The composition of claim 1, wherein the neutron capture agent constitutes between 15%-85% of the total weight of the BPMO.

4. The composition of claim 1, wherein the neutron capture agent comprises the boron isotope $^{10}$B.

5. The composition of claim 1, wherein the neutron capture agent comprises the lithium isotope $^{6}$Li.

6. The composition of claim 1, wherein the neutron capture agent comprises the cadmium isotope $^{113}$Cd.

7. The composition of claim 1, wherein the neutron capture agent comprises the samarium isotope $^{149}$Sm.

8. The composition of claim 1, wherein the neutron capture agent comprises the gadolinium isotope $^{157}$Gd.

9. The composition of claim 1, wherein the neutron capture agent comprises $^{10}$B-4 borono L-phenylalanine ($^{10}$BPA).

10. A kit comprising the composition of claim 1, wherein the kit further comprises at least one container and at least one label.

11. A dosage unit form comprising the composition of claim 1, wherein the dosage unit form further comprises a single injection.

12. A method of performing neutron capture therapy in the treatment of human cancer comprising:
a) loading a biodegradable periodic mesoporous organosilica (BPMO) nanomaterial with neutron capture agent, wherein the BPMO is modified with a disulfide bond, a tetrasulfide bond, or a protease sensitive bond and wherein the BPMO surface is modified with phosphonate;
b) injecting the loaded BPMO into a human cancer tumor, whereby said loaded BPMO accumulates into a human cancer tumor cell; and
c) irradiating the loaded BPMO with neutrons.

13. The method of claim 12, wherein the irradiation comprises epithermal neutrons.

14. The method of claim 13, wherein the irradiation triggers neutron activation.

15. The method of claim 13, wherein the neutron capture agent is selected from the group consisting of the boron isotope $^{10}$B, the lithium isotope $^{6}$Li, the cadmium isotope $^{113}$Cd, the samarium isotope $^{149}$Sm, and the gadolinium isotope $^{157}$Gd.

* * * * *